US009089691B2

(12) United States Patent
Libbus et al.

(10) Patent No.: US 9,089,691 B2
(45) Date of Patent: Jul. 28, 2015

(54) STIMULATOR FOR AURICULAR BRANCH OF VAGUS NERVE

(75) Inventors: Imad Libbus, St. Paul, MN (US); Julia Moffitt, North Liberty, IA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1273 days.

(21) Appl. No.: 11/005,703

(22) Filed: Dec. 7, 2004

(65) Prior Publication Data

US 2006/0122675 A1 Jun. 8, 2006

(51) Int. Cl.
*A61N 1/36* (2006.01)
*A61N 1/05* (2006.01)

(52) U.S. Cl.
CPC .......... *A61N 1/0551* (2013.01); *A61N 1/36017* (2013.01); *A61N 1/36114* (2013.01); *A61N 1/0556* (2013.01)

(58) Field of Classification Search
CPC ............ A61N 1/0551; A61N 1/36017; A61N 1/36032; A61N 1/36114
USPC ........... 607/17, 40, 45–46; 600/382, 386, 379
See application file for complete search history.

(56) References Cited

U.S. PATENT DOCUMENTS

| | | | |
|---|---|---|---|
| 4,503,863 A | | 3/1985 | Katims |
| 4,865,048 A | | 9/1989 | Eckerson |
| 4,966,164 A | * | 10/1990 | Colsen et al. .................. 607/72 |
| 4,989,605 A | | 2/1991 | Rossen |
| 5,197,471 A | * | 3/1993 | Otero ............................ 600/392 |
| 5,263,480 A | | 11/1993 | Wernicke et al. |
| 5,458,625 A | | 10/1995 | Kendall |
| 5,514,175 A | | 5/1996 | Kim et al. |
| 5,556,421 A | | 9/1996 | Prutchi et al. |
| 5,673,692 A | | 10/1997 | Schulze et al. |
| 5,891,181 A | | 4/1999 | Zhu |
| 6,473,644 B1 | | 10/2002 | Terry, Jr. et al. |

(Continued)

FOREIGN PATENT DOCUMENTS

| | | |
|---|---|---|
| JP | 54-070685 A | 6/1979 |
| JP | 7-116190 A | 5/1995 |

(Continued)

OTHER PUBLICATIONS

"International Search Report and Written Opinion for Application No. PCT/US2005/042208, Date Mailed Apr. 18, 2006", 16 Pages.

(Continued)

*Primary Examiner* — Eric D. Bertram
(74) *Attorney, Agent, or Firm* — Schwegman Lundberg & Woessner, P.A.

(57) ABSTRACT

Devices and methods to stimulate the auricular branch of the vagus nerve are provided. Various device embodiments comprise a lead, a neural stimulation circuit, and a controller. The lead has a neural stimulation electrode. The neural stimulation circuit is connected to the lead to deliver a neural stimulation signal adapted to stimulate the auricular nerve branch using the neural stimulation electrode. The controller is connected to the neural stimulation circuit and is adapted to control delivery of the neural stimulation signal from the neural stimulation circuit to provide a vagal stimulation therapy. In various embodiments, the electrode is adapted to be placed in an external auditory canal. In various embodiments, the electrode includes a transcutaneous neural stimulation electrode adapted to be placed behind an ear.

46 Claims, 8 Drawing Sheets

(56) References Cited

U.S. PATENT DOCUMENTS

| | | | |
|---|---|---|---|
| 7,218,964 B2 | 5/2007 | Hill et al. | |
| 7,277,761 B2 | 10/2007 | Shelchuk | |
| 7,536,227 B1 | 5/2009 | Poore et al. | |
| 2002/0072781 A1* | 6/2002 | Lattner et al. | 607/42 |
| 2002/0091418 A1 | 7/2002 | Hauser et al. | |
| 2002/0107553 A1 | 8/2002 | Hill et al. | |
| 2002/0143369 A1 | 10/2002 | Hill et al. | |
| 2002/0165586 A1 | 11/2002 | Hill et al. | |
| 2003/0195588 A1 | 10/2003 | Fischell et al. | |
| 2004/0215289 A1 | 10/2004 | Fukui | |
| 2005/0102006 A1* | 5/2005 | Whitehurst et al. | 607/46 |
| 2005/0143779 A1 | 6/2005 | Libbus | |
| 2005/0165460 A1* | 7/2005 | Erfan | 607/57 |
| 2006/0041283 A1* | 2/2006 | Gelfand et al. | 607/44 |
| 2008/0288016 A1 | 11/2008 | Amurthur et al. | |

FOREIGN PATENT DOCUMENTS

| | | |
|---|---|---|
| JP | 8-322825 A | 12/1996 |
| JP | 11-500930 A | 1/1999 |
| JP | 2003-511163 A | 3/2003 |
| JP | 2003-520094 A | 7/2003 |
| JP | 2003-325636 A | 11/2003 |
| JP | 2004180988 A | 7/2004 |
| JP | 2004-275427 A | 10/2004 |
| JP | 2004-533297 A | 11/2004 |
| JP | 2006-524106 A | 10/2006 |
| WO | WO-9216257 A1 | 10/1992 |
| WO | WO-96/25978 A1 | 8/1996 |
| WO | WO-01/26729 A1 | 4/2001 |
| WO | WO-01/52731 A1 | 7/2001 |
| WO | WO-02/096512 A1 | 12/2002 |
| WO | WO-03/076008 A1 | 9/2003 |
| WO | WO-04/000413 A2 | 12/2003 |
| WO | WO-04000413 A2 | 12/2003 |
| WO | WO-2004069328 A2 | 8/2004 |
| WO | WO-2004/091719 A2 | 10/2004 |
| WO | WO-2006122148 A2 | 11/2006 |
| WO | WO-2007134804 A1 | 11/2007 |
| WO | WO-2008143814 A2 | 11/2008 |
| WO | WO-2008143814 A3 | 11/2008 |

OTHER PUBLICATIONS

Libbus, I., et al., "Method and Apparatus for Synchronizing Neural Simulation to Cardiac Cycles", U.S. Appl. No. 11/099,141, filed Apr. 5, 2005.
Libbus, I., et al., "System and Method for Closed-Loop Neural Stimulation", U.S. Appl. No. 10/992,319, filed Nov. 18, 2004.
Nolan, James, "Prospective study of heart rate variability and mortality in chronic heart failure: results of the United Kingdom heart failure evaluation and assessment of risk trial (UK-heart).", *Circulation*, 98(15), (Oct. 13, 1998), 1510-1516.
Sigurdsson, Axel, "The role of neurohormonal activation in chronic heart failure and postmyocardial infarction", *American Heart Journal*, 132 (1 Pt 2 Su), (Jul. 1996), 229-234.
Vanoli, Emilio, "Vagal stimulation and prevention of sudden death in conscious dogs with a healed myocardial infarction", *Circulation Research*, 68(5), (May 1991), 1471-81.
Zamotrinsky, A. V., et al., "Vagal neurostimulation in patients with coronary artery disease", *Autonomic Neuroscience-Basic & Clinical*, 88(1-2), (Apr. 12, 2001), 109-16.
"U.S. Appl. No. 11/749,500, Non Final Office Action mailed Nov. 17, 2010", 8 pgs.
"U.S. Appl. No. 11/749,500, Response filed Sep. 20, 2010 to Restriction Requirement mailed Aug. 18, 2010", 6 pgs.
"U.S. Appl. No. 11/749,500, Advisory Action mailed Apr. 4, 2012", 3 pgs.
"Japanese Application Serial No. 2007-545498, Office Action Response filed Mar. 12, 2012 to Office Action mailed Sep. 14, 2011", (w/ English Translation of Amended Claims), 20 pgs.
"International Application Serial No. PCT/US2008/006023, Invitation to Pay Additional Fees and Partial International Search Report mailed Aug. 5, 2008", 6 pgs.
"International Application Serial No. PCT/US2008/006023, International Search Report mailed Dec. 3, 2008", 6 pgs.
"International Application Serial No. PCT/US2008/006023, Written Opinion mailed Dec. 3, 2008", 9 pgs.
"European Application Serial No. 05 85 1959.6, Office Action Mailed Nov. 24, 2008", 3 pgs.
"European Application Serial No.—05851959.6, Office action Mailed Apr. 30, 2009", 3 pgs.
Huang, H Q, et al., "Improvement of blood pressure and left cardiac function in patients with hypertension by auricular acupuncture", *Zhong Xi Yi Jie He Za Zhi*, vol. 11, No. 11, [Article in Chinese with English Abstract], (Nov. 1991), 654-6, 643-4.
"U.S. Appl. No. 11/749,500 Restriction Requirement mailed Aug. 18, 2010", 8 pgs.
"European Application Serial No. 05851959.6, Office Action mailed Apr. 23, 2010", 4 pgs.
"European Application Serial No. 05851959.6, Response filed Mar. 30, 2009 to Office Action mailed Nov. 24, 2008", 15 pgs.
"European Application Serial No. 05851959.6, Response filed Sep. 2, 2010 to Communication dated Apr. 23, 2010", 5 pgs.
"European Application Serial No. 05851959.6, Response filed Sep. 21, 2009 to Office Action mailed Apr. 30, 2009", 10 pgs.
"International Application Serial No. PCT/US2005/042208, International Search Report mailed Apr. 18, 2006", 5 pgs.
"International Application Serial No. PCT/US2005/042208, Written Opinion mailed Apr. 18, 2006", 9 pgs.
"Japanese Application Serial No. 2007-545498, Amendment filed Nov. 20, 2008", (w/ English Translation of Amended Claims), 18 pgs.
"U.S. Appl. No. 11/749,500, Response filed Mar. 19, 2012 to Final Office Action mailed Feb. 2, 2012", 12 pgs.
"U.S. Appl. No. 11/749,500, Final Office Action mailed Feb. 2, 2012", 14 pgs.
"Japanese Application Serial No. 2010-508384, Office Action mailed Dec. 19, 2011", (w/ English Translation), 10 pgs.
"Japanese Application Serial No. 2010-508384, Response filed Mar. 16, 2012 to Office Action mailed Dec. 19, 2011", (w/ English Translation of Amended Claims), 9 pgs.
"U.S. Appl. No. 11/749,500, Response filled Jul. 27, 2011 to Final office Action mailed Apr. 28, 2011", 11 pgs.
"U.S. Appl. No. 11/749,500, Advisory Action mailed Jul. 15, 2011", 3 pgs.
"U.S. Appl. No. 11/749,500, Final Office Action mailed Apr. 28, 2011", 10 pgs.
"U.S. Appl. No. 11/749,500, Response filed Feb. 16, 2011 to Non Final Office Action mailed Nov. 17, 2010", 8 pgs.
"U.S. Appl. No. 11/749,500, Response filed Jun. 30, 2011 to Final Office Action mailed Apr. 28, 2011", 11 pgs.
"U.S. Appl. No. 11/749,500, Amendment and Response filed Nov. 22, 2011 to Non Final Office Action mailed Aug. 22, 2011", 11 pgs.
"U.S. Appl. No. 11/749,500, Non Final Office Action mailed Aug. 22, 2011", 15 pgs.
"Japanese Application Serial No. 2007-545498, Office Action mailed Sep. 14, 2011", 6 pgs.
"U.S. Appl. No. 11/749,500 , Response filed Aug. 9, 2012 to Non Final Office Action mailed May 10, 2012", 9 pgs.
"U.S. Appl. No. 11/749,500, Examiner Interview Summary mailed Aug. 14, 2012", 3 pgs.
"U.S. Appl. No. 11/749,500, Final Office Action mailed Nov. 8, 2012", 11 pgs.
"U.S. Appl. No. 11/749,500, Final Office Action mailed Nov. 22, 2013", 13 pgs.
"U.S. Appl. No. 11/749,500, Non Final Office Action mailed May 2, 2013", 12 pgs.
"U.S. Appl. No. 11/749,500, Non Final Office Action mailed May 10, 2012", 11 pgs.
"U.S. Appl. No. 11/749,500, Notice of Allowance mailed Feb. 3, 2014", 8 pgs.
"U.S. Appl. No. 11/749,500, Response filed Aug. 2, 2013 to Non Final Office Action mailed May 2, 2013", 11 pgs.

(56) References Cited

OTHER PUBLICATIONS

"U.S. Appl. No. 11/749,500, Response filed Jan. 21, 2014 to Final Office Action mailed Nov. 22, 2013", 10 pgs.
"U.S. Appl. No. 11/749,500, Response filed Feb. 8, 2013 to Final Office Action mailed Nov. 8, 2012", 9 pgs.
"Japanese Application Serial No. 2007-545498, Examiners Decision of Final Refusal mailed Jun. 11, 2012", With English Translation, 9 pgs.
"Japanese Application Serial No. 2010-508384, Examiners Decision of Final Refusal mailed May 17, 2012", With English Translation, 9 pgs.

* cited by examiner

STIMULATOR FOR AURICULAR BRANCH OF VAGUS NERVE

TECHNICAL FIELD

This application relates generally to medical devices and, more particularly, to systems, devices and methods to stimulate nerves.

BACKGROUND

A reduced autonomic balance during heart failure has been shown to be associated with left ventricular dysfunction and increased mortality. This reduced autonomic balance increases sympathetic and decreases parasympathetic cardiac tone. Direct stimulation of the vagal parasympathetic fibers has been shown to reduce heart rate via activation of the parasympathetic nervous system and indirect inhibition of the sympathetic nervous system. Some data indicate that increasing parasympathetic tone and reducing sympathetic tone may protect the myocardium from further remodeling and predisposition to fatal arrhythmias following myocardial infarction; and some data indicates that chronic stimulation of the vagus nerve may protect the myocardium following cardiac ischemic insult. However, implantation of electrodes is an invasive procedure, and it can be difficult to immediately implant electrodes after a myocardial infarction.

The auricular nerve is a branch of the vagus nerve that passes near the external auditory canal immediately behind the ear. Stimulation of this nerve branch depolarizes the vagus and elicits bradycardia. Needle puncture electrodes have been used to stimulate the auricular branch of the vagus nerve. The needle puncture electrodes punctured the skin to a depth of 0.1-0.3 mm in the area situated near the auditory passage that contains endings of the nerve auricularis. The neural stimulation applied by these needle puncture electrodes to the auricular branch improved anginal symptoms, improved coronary blood flow, increased ejection fraction and reduced the incidence of developing congestive heart failure (CHF).

SUMMARY

Various embodiments of the present subject matter relate to device to stimulate an auricular nerve branch of the vagus nerve. In various embodiments, the device comprises a lead, a neural stimulation circuit, and a controller.

In various device embodiments, the lead has a neural stimulation electrode adapted to be placed in an external auditory canal to stimulate the auricular nerve branch. The neural stimulation circuit is connected to the lead to deliver a neural stimulation signal adapted to stimulate the auricular nerve branch using the neural stimulation electrode. The controller is connected to the neural stimulation circuit and is adapted to control delivery of the neural stimulation signal from the neural stimulation circuit to provide a vagal stimulation therapy.

In various device embodiments, the lead has a transcutaneous neural stimulation electrode to be placed behind an ear to transcutaneously stimulate the auricular nerve branch. The neural stimulation circuit is connected to the lead to deliver a neural stimulation signal adapted to stimulate the auricular nerve branch using the neural stimulation electrode. The controller is connected to the neural stimulation circuit and adapted to control delivery of the neural stimulation signal from the neural stimulation circuit to provide a vagal stimulation therapy.

Various device embodiments comprise at least one port to connect at least one lead, a feedback circuit and a controller. The lead(s) include at least one neural stimulation electrode and at least one physiology sensor. The neural stimulation circuit is connected to the port(s) to selectively deliver a neural stimulation signal to the neural stimulation electrode to stimulate the auricular nerve branch. The feedback circuit is connected to the port(s) to receive a feedback signal from the physiology sensor(s). The controller is connected to the neural stimulation circuit and adapted to deliver the neural stimulation signal to the neural stimulation electrode, and is connected to the feedback circuit and adapted to adjust the neural stimulation signal in response to the feedback signal.

Various embodiments of the present subject matter relate to a method to provide vagal stimulation. According to various embodiments of the method, a non-invasive neural stimulation electrode is positioned proximate to an auricular nerve branch of a vagus nerve, and a neural stimulation signal is applied to the electrode to transcutaneously stimulate the auricular nerve branch.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1B:
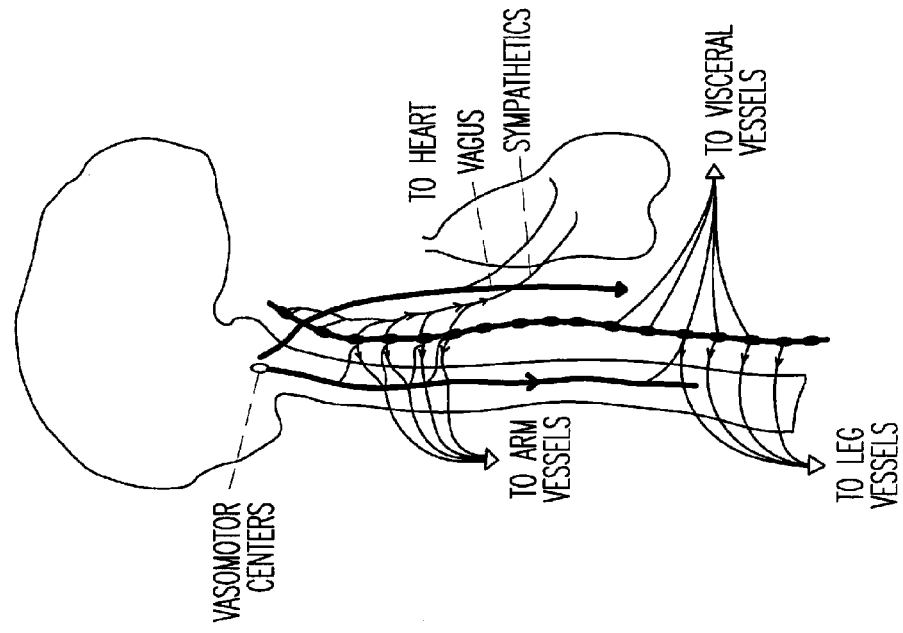
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter provides systems and methods to stimulate the auricular branch of the vagus nerve. Vagal stimulation simultaneously increases parasympathetic and decreases sympathetic myocardial tone, and reduces myocardial exposure to epinephrine which reducing myocardial death and fibrosis. A number of proposed therapies involve vagal stimulation. Vagal stimulation therapy is believed to prevent further remodeling or predisposition to fatal arrhythmias in post-MI patients, to help restore autonomic balance and increase HRV (heart rate variability), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development of congestive heart failure (CHF) following MI.

Various embodiments of the present subject matter non-invasively stimulate the auricular nerve branch. For example, various embodiments stimulate the auricular branch of the vagus nerve within the auditory canal using a bipolar electrode attached to an external stimulator, and various embodiments stimulate the auricular branch of the vagus nerve using transcutaneous electrodes, such as patch electrodes, placed on the skin behind the ear over or otherwise proximate to the auricular nerve to elicit depolarization of the nerve. An implantable pulse generator may not be needed. A greater range of frequency and voltage limitations may be used to administer the stimulation within the physician's office.

Various embodiments of the present subject matter stimulate the auricular nerve branch in a minimally-invasive manner. For example, various embodiments implant a stimulating electrode subcutaneously immediately over the auricular nerve. Various embodiments use an implantable device to provide neural stimulation signal to the implanted electrodes, and various embodiments use a magnet to activate the neural stimulation therapy provided by the implantable device.

Various embodiments provide closed loop control of the neural stimulation. For example, various embodiments deliver the stimulation via closed loop system integrated to the patients ECG or based on other physiologic signals such as blood pressure, heart rate and the like. For example, some neural stimulator embodiments are integrated with an ECG monitor. Some neural stimulator embodiments directly sense heart rate from the carotid artery. Some neural stimulator embodiments are integrated with a blood pressure monitor, and some sense blood pressure from the carotid artery. Various embodiments deliver the stimulation via an open loop system, such as may be provided by short term therapy, and intermittent or periodic therapies of relative short duration, for example.

Various embodiments allow a patient to activate the neural stimulation. Various embodiments permit a patient to initiate the stimulation of the auricular nerve with predetermined stimulation parameters. Such patient-activated devices can be used to provide as-needed vagal stimulation for angina therapy, for example.

Various embodiments provide systems and methods to quickly stimulate the vagus nerve following MI or in a heart failure patient, thus protecting the myocardium from further remodeling and arrhythmogenesis. The non-invasive nature of these approaches allow it to be immediately administered post-MI (myocardial infarction) or during ischemic episodes. Data indicates that intermittent stimulation, such as stimulation for 15 minutes per day for 10 days, may be effective at reducing cardiac sympathetic tone.

Transcutaneous and some superficial subcutaneous approaches to peripheral nerve stimulation are capable of avoiding direct neural contact with a stimulating electrode, thereby reducing problems associated with neural inflammation and injury commonly associated with direct contact electrodes.

Provided below is a discussion of Neural Physiology, Neural Stimulation Device/System Embodiments, and Method Embodiments to Stimulate the Auricular Nerve Branch.

Neural Physiology

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example. The nervous system includes afferent nerves, which transmit neural signals from the body (e.g. vascular control, body organs, and the like) to the central nervous system (CNS), and includes efferent nerves which transmit neural signals from the CNS out to the body.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
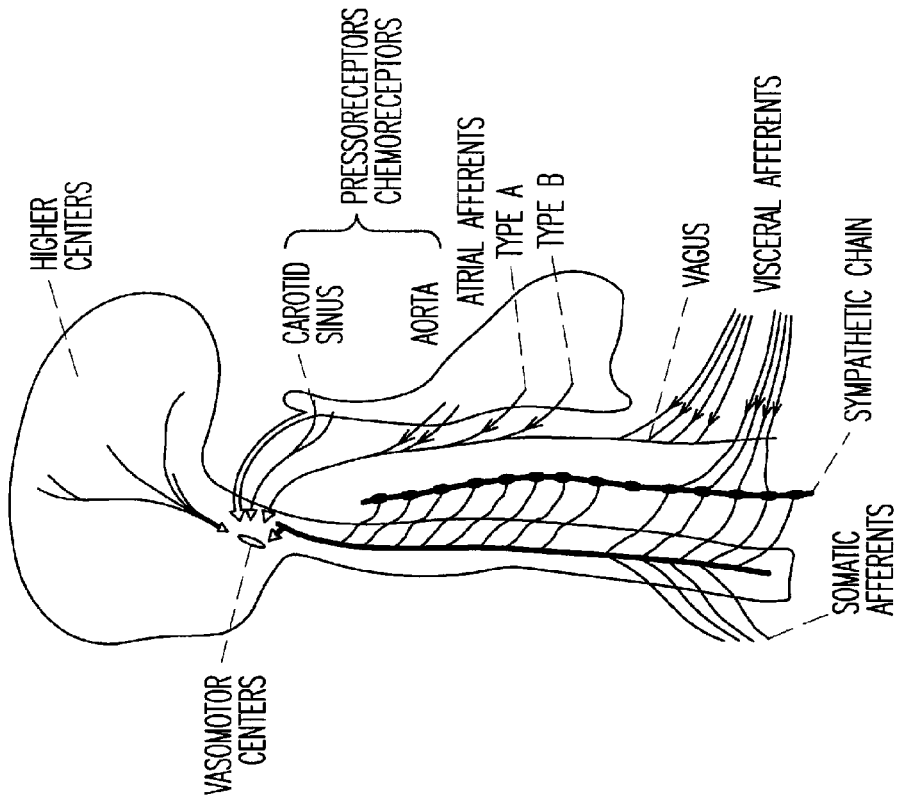

FIGS. 1A and 1B illustrate neural mechanisms for peripheral vascular control. The vagus nerve is illustrated in these figures. FIG. 1A generally illustrates afferent nerves to vasomotor centers. An afferent nerve conveys impulses toward a nerve center (CNS). A vasomotor center relates to nerves that dilate and constrict blood vessels to control the size of the blood vessels. FIG. 1B generally illustrates efferent nerves from vasomotor centers. An efferent nerve conveys impulses away from a nerve center (CNS).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve is an afferent nerve, such that the neural stimulation is transmitted to the CNS. Vagal stimulation simultaneously increases parasympathetic and decreases sympathetic activity, and is believed to prevent further remodeling or predisposition to fatal arrhythmias in post-MI patients, to help restore autonomic balance and increase HRV (heart rate variability), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development of congestive heart failure (CHF) following MI.

The auricular nerve of the vagus nerve, which includes the greater auricular nerve and the lesser auricular nerve, originates from the cervical plexus. The greater auricular nerve innervates the surfaces of the outer ear, and the skin over the parotid gland and mastoid process. The parotid gland is a salivary gland found in front of the ears and that extends to the area beneath the earlobe along the lower border of the jawbone. The mastoid process is the conical prominence of the temporal bone of the human skull behind the ear.

Neural Stimulator Device/System Embodiments

Figure 2A:
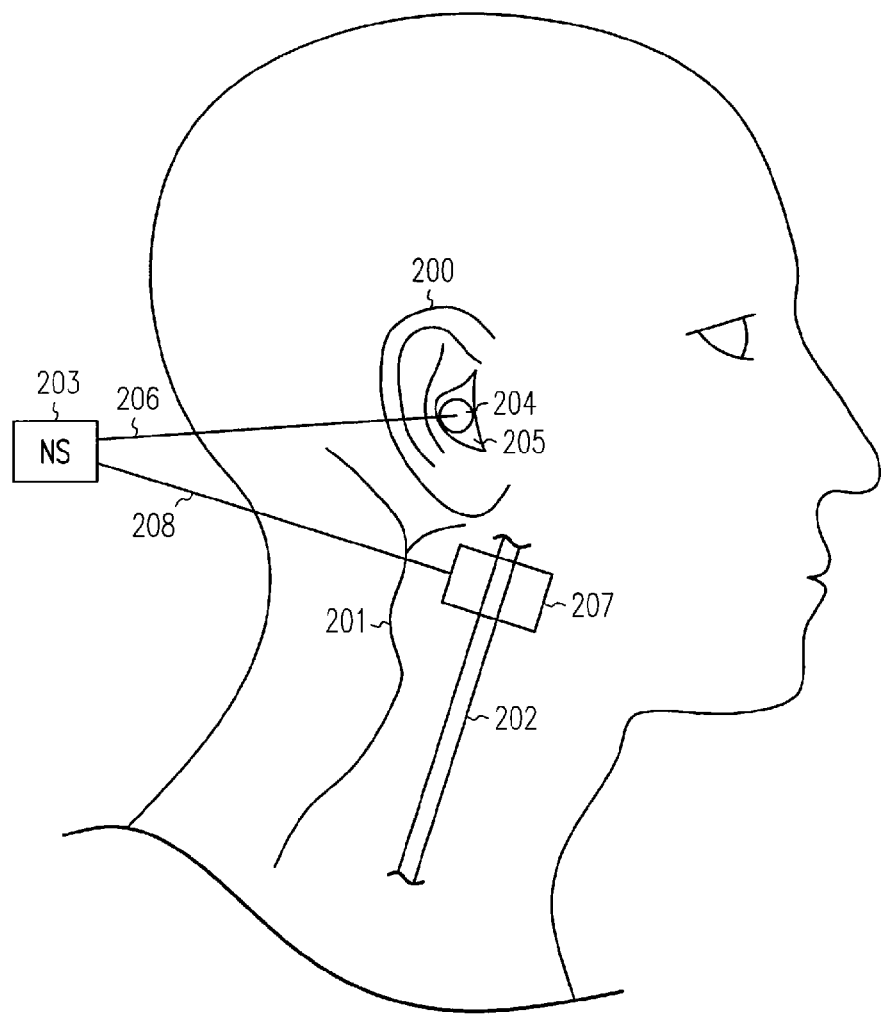
FIGS. 2A and 2B illustrate various embodiments of a neural stimulator with a neural stimulator electrode adapted to be positioned in the external auditory canal to stimulate the auricular nerve branch.
Figure 2B:
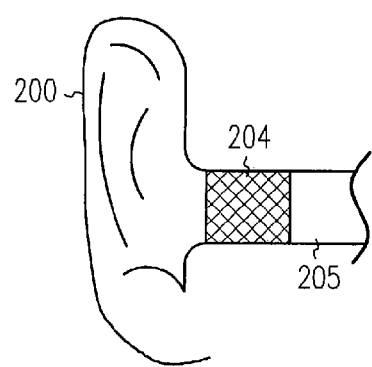

FIGS. 2A and 2B illustrate various embodiments of a neural stimulator with a neural stimulator electrode adapted to be positioned in the external auditory canal to stimulate the auricular nerve branch. FIG. 2A illustrates a human ear 200, an auricular nerve branch 201 of a vagus nerve, and a carotid artery 202. FIG. 2A further illustrates a neural stimulation device 203 with neural stimulation electrode 204 (e.g. bipolar electrode) adapted to be placed in an external auditory canal 205 of the human ear. The neural stimulation electrode is connected to the neural stimulation device by a lead 206. The neural stimulation device is capable of providing appropriate an neural stimulation to the neural stimulation electrode to elicit depolarization of the auricular nerve branch.

According to various embodiments, the illustrated neural stimulation device 203 functions as an open loop stimulation system. In the open loop system, the neural stimulation is applied based on a predetermined or programmed set of parameters. Thus, for example, various open loop embodiments stimulate with a predetermined waveform (e.g. white noise, square, sinusoidal, triangular, and the like), magnitude, frequency, burst frequency and duration. Some embodiments provide intermittent stimulation and some embodiments provide periodic stimulation. Periodic stimulation relates to stimulation at regular intervals. Intermittent stimulation relates to applying stimulation during some times but not at other times. Intermittent stimulation does not necessarily refer to providing stimulation at regular intervals.

According to various embodiments, the illustrated neural stimulation device 203 functions as a closed loop stimulation system. In the closed loop system, physiology signals are sensed. The neural stimulation device appropriately adjusts the applied neural stimulation therapy based on the sensed physiology sensors. Examples of physiology sensors include sensors to detect heart rate and blood pressure, and further includes ECG monitors. FIG. 2A also illustrates an embodiment with a sensor 207 positioned over the carotid artery 202 and connected to the neural stimulation device 203 via a lead 208. Various embodiments sense heart rate from the sensor 207, and various embodiments sense blood pressure from the sensor 207. Various embodiments control the stimulation of the auricular nerve branch based on ECG signals.

FIG. 2B illustrates a neural stimulation electrode 204 placed in the external auditory canal 205. Various embodiments provide an expandable, stent-like electrode placed in the auditory canal. Various embodiments incorporates the electrode in an expandable foam, such as an ear plug, to quickly place the electrode against a surface of the external auditory canal. In some embodiments, the housing of the neural stimulation device is conductive, and functions as the electrode in the auditory canal.

Figure 3:
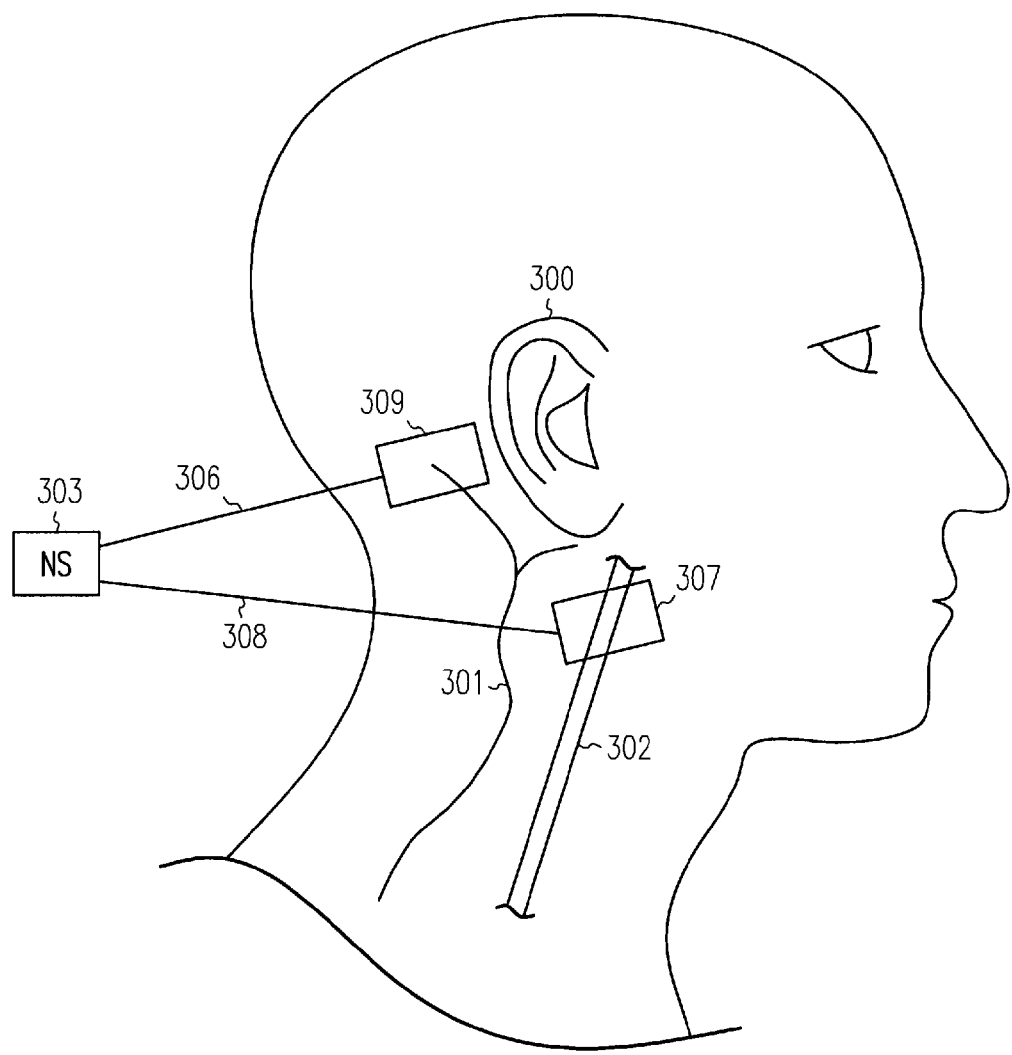
FIG. 3 illustrates various embodiments of a neural stimulator with a transcutaneous neural stimulation electrode to be placed behind an ear to transcutaneously stimulate the auricular nerve branch.

FIG. 3 illustrates various embodiments of a neural stimulator with a transcutaneous neural stimulation electrode to be placed behind an ear to transcutaneously stimulate the auricular nerve branch. FIG. 3 illustrates a human ear 300, an auricular nerve branch 301 of a vagus nerve, and a carotid artery 302. FIG. 3 further illustrates a neural stimulation device with transcutaneous neural stimulation electrode 309 adapted to be placed on the skin of the head behind the human ear. In various embodiments, the electrode includes a patch electrode, such as the transcutaneous electrical nerve stimulation (TENS) electrodes. The transcutaneous neural stimulation is supplied from the electrode on the surface of the skin, through the skin, and to the auricular nerve branch. The neural stimulation electrode is connected to the neural stimulation device 303 by a lead 306. The neural stimulation device is capable of providing appropriate an neural stimulation to the neural stimulation electrode to elicit depolarization of the auricular nerve branch. In some embodiments, the housing of the neural stimulation device is conductive, and functions as the transcutaneous electrode.

According to various embodiments, the illustrated neural stimulation device 303 functions as a open loop stimulation system. In the open loop system, the transcutaneous neural stimulation from the patch electrode is applied based on a predetermined or programmed set of parameters. Thus, for example, various open loop embodiments stimulate with a predetermined waveform (e.g. white noise, square, sinusoidal, triangular, and the like), magnitude, frequency, burst frequency and duration. Some embodiments provide intermittent stimulation and some embodiments provide periodic stimulation.

According to various embodiments, the illustrated neural stimulation device 303 functions as a closed loop stimulation system. In the closed loop system, physiology signals are sensed. The neural stimulation device appropriately adjusts the applied neural stimulation therapy based on the sensed physiology sensors. Examples of physiology sensors include sensors to detect heart rate and blood pressure, and further includes ECG sensors. FIG. 3 also illustrates an embodiment with a sensor 307 positioned over the carotid artery 302 connected to the neural stimulation device by a lead 308. Various embodiments sense heart rate from the sensor, and various embodiments sense blood pressure from the sensor. Various embodiments control the stimulation of the auricular nerve branch based on ECG signals.

Figure 4:
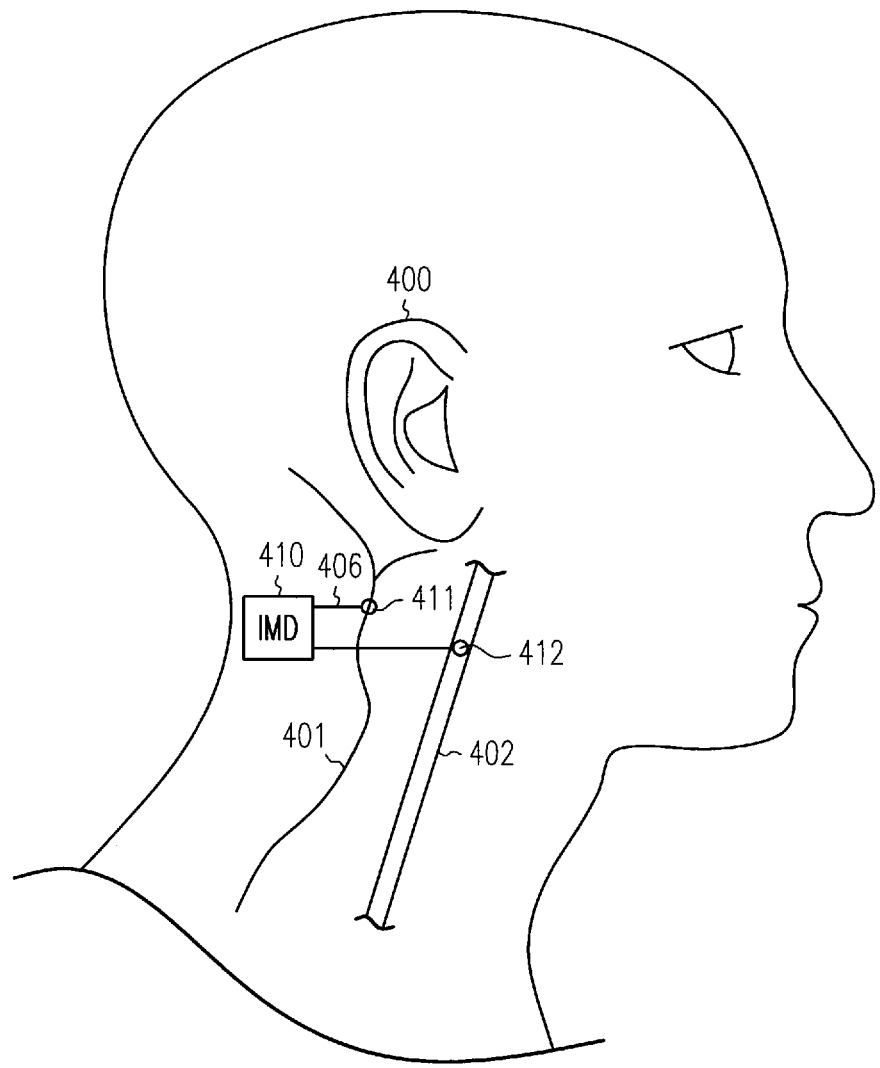
FIG. 4 illustrates various embodiments of an implantable neural stimulator with a neural stimulation electrode to stimulate the auricular nerve branch.

FIG. 4 illustrates various embodiments of an implantable neural stimulator with a neural stimulation electrode to stimulate the auricular nerve branch. FIG. 4 illustrates a human ear 400, an auricular nerve branch 401 of a vagus nerve, and a carotid artery 402. FIG. 4 further illustrates an implantable medical device (IMD) 410, or an implantable neural stimulation device, adapted to be subcutaneously implanted in a minimally-invasive procedure. In various embodiments, for example, the neural stimulation electrode includes a nerve cuff electrode 411. The neural stimulation electrode is connected to the neural stimulation device by a lead 406, which is positioned subcutaneously between the electrode and the neural stimulation device. In some embodiments, the housing of the neural stimulation device is conductive, and functions as the subcutaneous electrode. The neural stimulation device is capable of providing an appropriate neural stimulation to the neural stimulation electrode to elicit depolarization of the auricular nerve branch.

According to various embodiments, the illustrated neural stimulation device 410 functions as a open loop stimulation system. In the open loop system, the neural stimulation is applied based on a predetermined or programmed set of parameters. Thus, for example, various open loop embodiments stimulate with a predetermined waveform (e.g. white noise, square, sinusoidal, triangular, and the like), magnitude, frequency, burst frequency and duration. Some embodiments provide intermittent stimulation and some embodiments provide periodic stimulation.

According to various embodiments, the illustrated neural stimulation device 410 functions as a closed loop stimulation system. In the closed loop system, physiology signals are sensed. The neural stimulation device appropriately adjusts the applied neural stimulation therapy based on the sensed physiology sensors. Examples of physiology sensors include sensors to detect heart rate and blood pressure. FIG. 4 also illustrates an embodiment with a sensor 412 positioned proximate to the carotid artery 402. Various embodiments sense heart rate from the sensor, and various embodiments sense blood pressure from the sensor. Various embodiments control the stimulation of the auricular nerve branch based on ECG signals. Various embodiments wirelessly communicate the ECG signals, or information derived from the ECG signals, from an external ECG monitor to the implantable neural stimulation device for use to adjust the applied neural stimulation.

Figure 5:
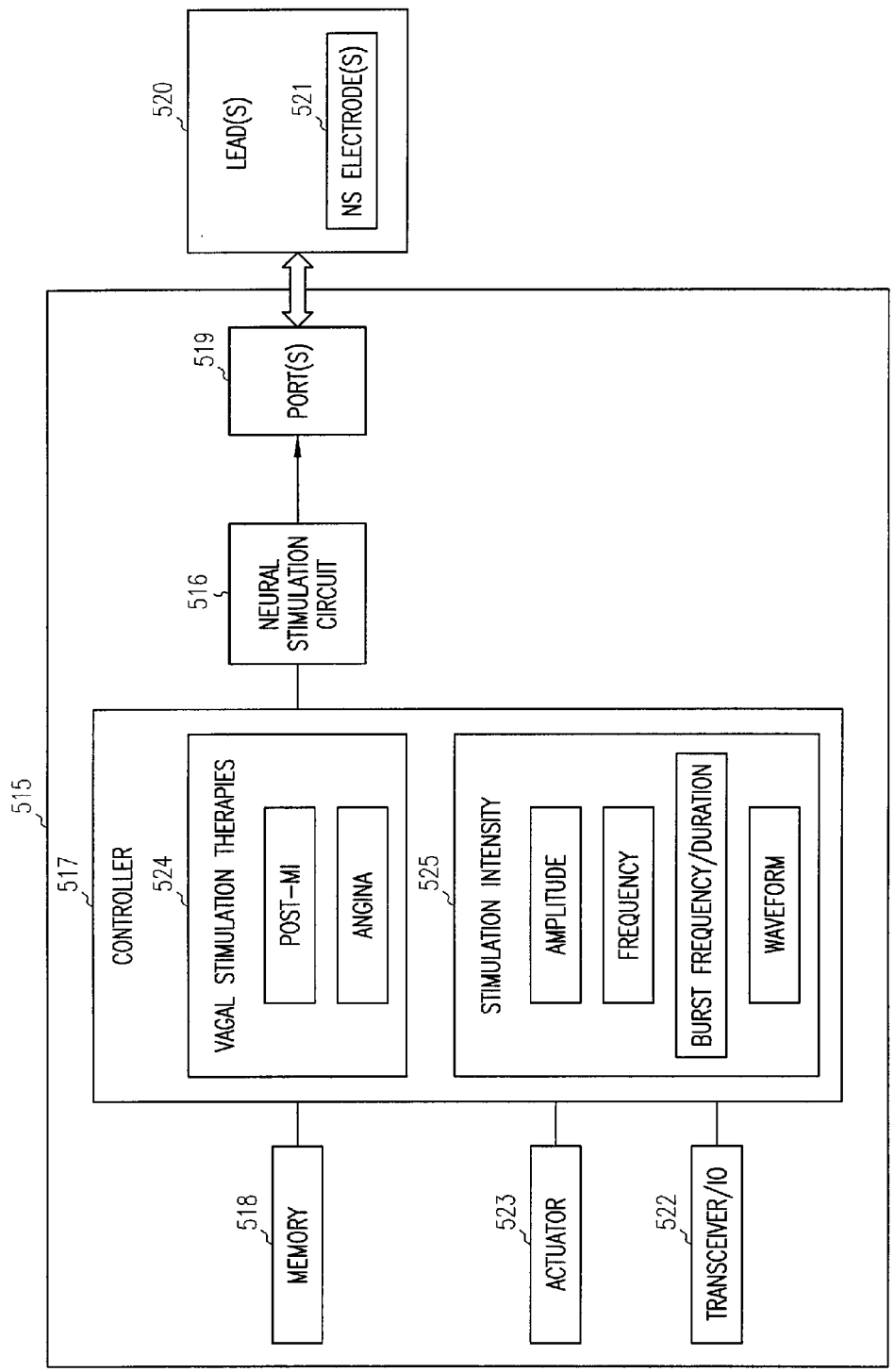
FIG. 5 illustrates various embodiments of a neural stimulator to stimulate the auricular nerve branch in an open loop stimulation system.

FIG. 5 illustrates various embodiments of a neural stimulator 515 to stimulate the auricular nerve branch in an open loop stimulation system. Such a neural stimulation device is capable of functioning as the open loop embodiments of stimulators 203, 303, and 410 in FIGS. 2A 3, and 4. The illustrated neural stimulator embodiment 515 includes a neural stimulation circuit 516, a controller 517, and memory 518. The illustrated embodiment further includes at least one port 519 to connect to at least one lead 520. Thus, for example, the lead(s) 520 is/are capable of detaching from the device 515, and other leads are capable of being used with the device. The neural stimulation circuit 516 is connected to the port(s) 519 to provide a neural stimulation signal to at least one neural stimulation electrode 521 on the lead(s) 520 to elicit depolarization of the auricular nerve branch of the vagus nerve when an appropriate signal is provided to an appropriately-positioned neural stimulation electrode or electrodes. Some embodiments stimulate the auricular nerve branch using a single lead and a single electrode on the lead. However, multiple leads and multiple electrodes on the leads can be used. In various embodiments, the neural stimulation electrode 521 is designed to be positioned in an external auditory canal, and the neural stimulation circuit is designed to be able to stimulate the auricular nerve branch using the electrode located in the external auditory canal. In various embodiments, the neural stimulation electrode 521 is designed to be a transcutaneous electrode, such as a patch electrode, positioned on the skin of the head behind the ear and over or otherwise proximate to the auricular nerve branch, and the neural stimulation circuit is designed to be able to stimulate the auricular nerve branch using the transcutaneous electrode located behind the ear. Both the auditory canal and behind the ear placements are non-invasive. An advantage of these non-invasive techniques is that the electrodes can be quickly positioned by a person who has minimal training, thus allowing vagal therapy to be quickly applied. Thus, for example, vagal therapy can be quickly applied in an emergency setting to begin post myocardial (post-MI) therapy. These embodiments also provide a quick, non-invasive way to treat angina or perform vagal stimulation as part of another therapy. In various embodiments, the neural stimulation electrode 521 is designed to be a superficial subcutaneous electrode, such as a cuff electrode, positioned around the auricular nerve branch, and the neural stimulation circuit is designed to be able to stimulate the auricular nerve branch using the subcutaneous electrode cuffed around the auricular nerve branch. In various embodiments, the electrode includes an electrode designed to pierce through the skin (such as a pin) and be proximate to the auricular nerve branch.

The illustrated neural stimulator 515 further includes a transceiver or other input/output (IO) circuit 522, and an actuator 523. The IO circuit allows the neural stimulator device to communicate with other devices, and thus can be used to program the neural stimulator device and/or upload historical neural stimulator data recorded over a period of time, for example. A wireless transceiver can be used to provide IO functions for both external and implantable devices. The actuator 523 provides a means for initiating a programmed therapy. Various actuator embodiments include a switch, such as mechanical, electrical, electronic and magnetic switches. The actuator can be triggered by a physician, emergency personal or a patient to initiate a preprogrammed therapy. Thus, in various embodiments, for example, a patient is capable of initiating angina therapy by positioning a magnet next to an implantable embodiment of the neural stimulator device.

The memory 518 includes computer-readable instructions that are capable of being operated on by the controller to perform functions of the device. Thus, in various embodiments, the controller is adapted to operate on the instructions to provide programmed vagal stimulation therapies 524 such as post-MI and angina therapies. Additionally, in various embodiments, the controller is adapted to set parameters of the neural stimulation signal and, in some embodiments, vary parameters of the neural stimulation signal to adjust the intensity of the neural stimulation, such as is generally illustrated by the stimulation intensity module 525. Some embodiments control and/or vary the waveform, amplitude, frequency, burst frequency and duration, and some embodiments control and/or adjust various combinations of two or more of the waveform, amplitude, frequency, burst frequency and duration. Examples of waveforms include sinusoidal, square, triangular, and "white noise" signals. A white noise signal mimics naturally-occurring neural activity. Various "open loop" systems vary the intensity of the neural stimulation according to a preprogrammed therapy to provide a desired affect. For example, some embodiments vary parameters of the neural stimulation signal to prevent or reduce neural adaptation to the neural stimulation signal.

Figure 6:
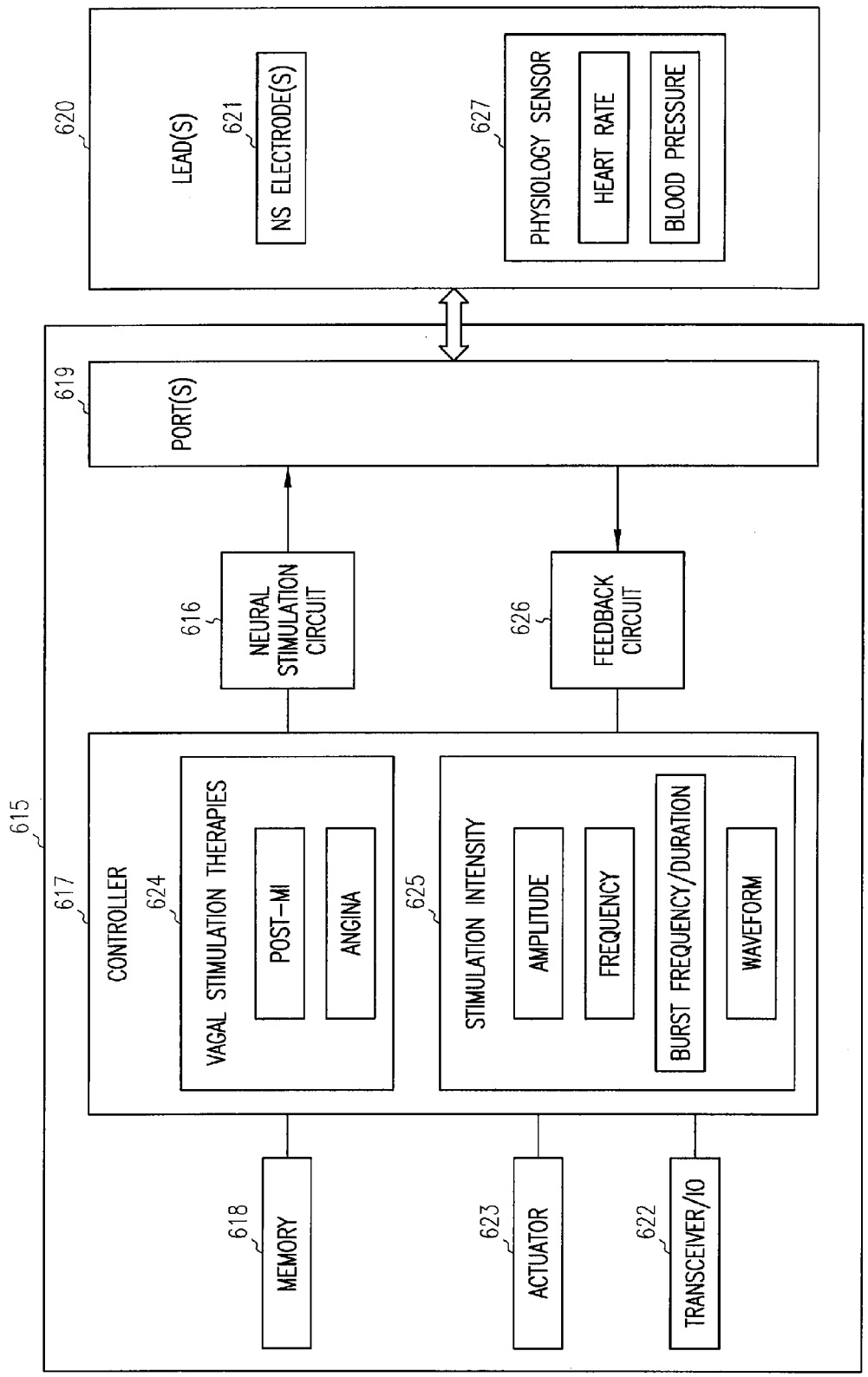
FIG. 6 illustrates various embodiments of a neural stimulator to stimulate the auricular nerve branch in a closed loop stimulation system.

FIG. 6 illustrates various embodiments of a neural stimulator to stimulate the auricular nerve branch in a closed loop stimulation system. Such a neural stimulation device is capable of functions as device 203, 303 and 410 in FIGS. 2A, 3 and 4, respectively. The illustrated neural stimulator embodiment 615 includes a neural stimulation circuit 616, a feedback circuit 626, a controller 617, and memory 618. The illustrated embodiment further includes at least one port 619 to connect to at least one lead 620. Thus, for example, the lead(s) is/are capable of detaching from the device, and other leads are capable of being used with the device. For example, one lead, which is connected to a first port, includes a neural stimulation electrode 621, and a second lead, which is connected to a second port, includes a physiology sensor 627. In another example, one lead, which is connected to one port, includes both a neural stimulation electrode 621 and a physiology sensor 627.

The neural stimulation circuit is connected to the port(s) to provide a neural stimulation signal to at least one neural stimulation electrode on the lead(s) to elicit depolarization of the auricular nerve branch of the vagus nerve when an appropriate signal is provided to an appropriately-positioned neural stimulation electrode. In various embodiments, the electrode is designed to be positioned in an external auditory canal, and the neural stimulation circuit is designed to be able to stimulate the auricular nerve branch using the electrode located in the external auditory canal. In various embodiments, the electrode is designed to be a transcutaneous electrode, such as a patch electrode, positioned on the skin of the head behind the ear and over or otherwise proximate to the auricular nerve branch, and the neural stimulation circuit is designed to be able to stimulate the auricular nerve branch using the transcutaneous electrode located behind the ear. Both the auditory canal and behind the ear placements are non-invasive. In various embodiments, the electrode is designed to be a superficial subcutaneous electrode, such as a cuff electrode, positioned around the auricular nerve branch, and the neural stimulation circuit is designed to be able to stimulate the auricular nerve branch using the subcutaneous electrode cuffed around the auricular nerve branch.

The feedback circuit 626 is connected to the port(s) to receive a signal from the physiology sensor 627. The sensor senses a physiology function that depends, at least in part, on vagal stimulation. Examples of such functions includes heart rate and blood pressure. Thus, various embodiments implement a heart rate sensor as the physiology sensor, and various embodiments implement a blood pressure sensor as the physiology sensor. The carotid artery runs proximate to the auricular nerve branch. Thus, various embodiments provide a sensor capable of directly detecting the heart rate from the carotid artery, and various embodiments provide a sensor capable of directly detecting blood pressure from the carotid artery. One example of such a sensor is an acoustic sensor adapted to sense blood flow. The sensed blood flow is capable of being used to determine blood pressure and/or heart rate. However, other sensor technology can be used. Transceiver 622, actuator 623, and memory 618 where previously discussed with respect to FIG. 5. This discussion is not repeated here for the sake of brevity.

The memory 618 includes computer-readable instructions that are capable of being operated on by the controller to perform functions of the device. Thus, in various embodiments, the controller is adapted to operate on the instructions to provide programmed vagal stimulation therapies 624 such as post-MI and angina therapies. Various "closed loop" systems vary the intensity of the neural stimulation, as generally illustrated by the stimulation intensity module 625, based on the sensed physiology signal received by the feedback circuit according to a preprogrammed therapy to provide a desired affect. Thus, the closed loop system is capable of reducing and increasing the neural stimulation intensity as appropriate to maintaining some measured physiological parameters within an upper and lower boundary during the vagal stimulation therapy.

Figure 7:
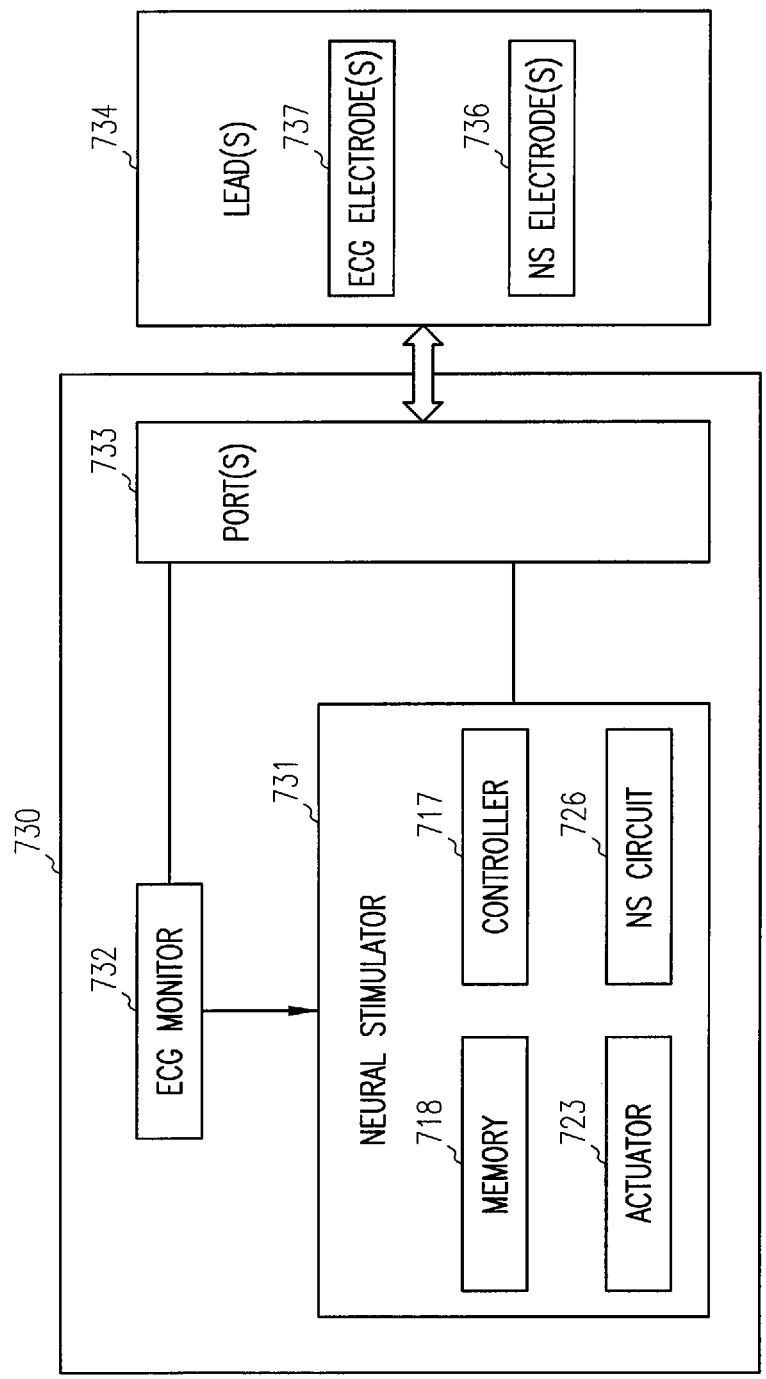
FIG. 7 illustrates various embodiments of a neural stimulator integrated with a ECG monitor to stimulate the auricular nerve branch in a closed loop system.

FIG. 7 illustrates various embodiments of a device or system 730 with a neural stimulator 731 integrated with a ECG monitor 732 to stimulate the auricular nerve branch in a closed loop system. The figure can illustrate either a device, with integrated ECG monitoring and neural stimulating capabilities, or a system with separate ECG and neural stimulation devices that cooperate together. The description that follows describes a device that includes an ECG monitor integrated with a neural stimulator to provide neural stimulation based on sensed ECG signals. Those of ordinary skill in the art will understand, upon reading and comprehending this disclosure, how to provide an ECG monitor and a neural stimulator that cooperate together to provide neural stimulation based on sensed ECG signals.

The illustrated embodiment includes at least one port 733 to connect to at least one lead 734. Thus, for example, the lead(s) is/are capable of detaching from the device, and other leads are capable of being used with the device. For example, one lead, which is connected to a first port, includes a neural stimulation electrode 736, and other leads, which are connected to other ports, include ECG electrodes 737 used to sense an ECG signal.

The illustrated neural stimulator includes a controller 717, neural stimulation circuit 726, memory 718 and actuator 723, as illustrated at 517, 516, 518, 523 in FIG. 5, respectively, and at 617, 616, 618, 623 in FIG. 6, respectively. The illustrated neural stimulator 731 receives feedback information from the ECG monitor 732, and adjusts the neural stimulation signal delivered to the neural stimulation electrode(s) based on the feedback information from the ECG monitor. In various embodiments, the feedback information from the ECG monitor includes heart rate. In various embodiments, the feedback information from the ECG monitor includes information derived from the morphology of the ECG signal. One example of a feedback parameter from the ECG monitor is a heart rate, such as can be determined by an R-R interval. In various embodiments, the neural stimulation is adjusted to obtain or maintain a desired heart rate (e.g. R-R interval). Vagal stimulation affects AV conduction. Thus, another example of a feedback parameter from the ECG monitor is a P-R interval. In various embodiments, the neural stimulation is adjusted to obtain or maintain a desired P-R interval.

Method Embodiments to Stimulate the Auricular Nerve Branch

Figure 8:
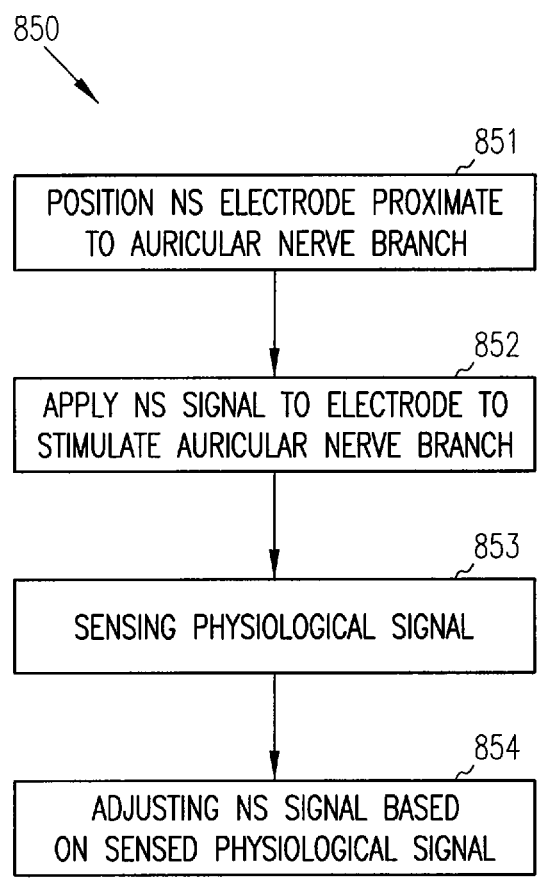
FIG. 8 illustrates a method to stimulate the auricular nerve branch, according to various embodiments of the present subject matter.

FIG. 8 illustrates a method to stimulate the auricular nerve branch, according to various embodiments of the present subject matter. The illustrated method 850 is capable of being stored as computer-readable instructions in a memory such as memory 518, 618, 718 and operated on by controller such as controller 517, 617, 717 in FIGS. 5, 6, 7 to provide a desired vagal stimulation therapy.

At 851, a neural stimulation electrode is positioned proximate to the auricular nerve branch. Various embodiments use a non-invasive technique to position the neural stimulation electrode, such as positioning a bipolar electrode in the external auditory canal or positioning a transcutaneous electrode behind the ear and over the auricular nerve branch. Various embodiments use a minimally-invasive technique to position the neural stimulation electrode, such as subcutaneously implanting a neural stimulator and an electrode to stimulate the auricular nerve branch. At 852, a neural stimulation signal is applied to stimulate the auricular nerve branch. In noninvasive embodiments, the neural stimulation signal transcutaneously stimulates the auricular nerve branch. In a subcutaneous implantation embodiment, a cuff electrode is placed around the auricular nerve branch to stimulate the nerve. In some external device embodiments, an electrode or electrodes are pierced through the skin to be proximate to the nerve.

Various embodiments provide a closed loop method to stimulate the auricular nerve branch. As illustrated at 853, a physiological signal is sensed. Various embodiments sense a heart rate. Various embodiments sense a blood pressure. Various embodiments sense the heart rate and/or blood pressure from the carotid artery. Various embodiments sense an electrocardiogram signal. At 854, the neural stimulation signal is adjusted based on the sensed physiological signal.

The methods illustrated in this disclosure are not intended to be exclusive of other methods within the scope of the present subject matter, whether the methods are disclosed specifically as methods or are disclosed as functions of the illustrated devices and system. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

One of ordinary skill in the art will understand that, the illustrated functional blocks in the diagrams can be identified as circuits and modules, and that the modules and other circuitry shown and described herein can be implemented using software, hardware, and combinations of software and hardware. As such, the term module is intended to encompass software implementations, hardware implementations, and software and hardware implementations.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A device, comprising:
    a lead with a neural stimulation electrode adapted to be placed past a conch of an outer ear into an external auditory canal to target an auricular nerve branch for neural stimulation, wherein the auricular nerve branch innervates surfaces of the outer ear and skin over a parotid gland and mastoid process near the outer ear, and wherein the neural stimulation electrode is configured to be appropriately placed within the external auditory canal effectively proximate to the outer ear near the auricular nerve branch to deliver stimulation from the external auditory canal out toward the auricular nerve branch;
    a neural stimulation circuit connected to the lead to deliver a neural stimulation signal from the neural stimulation electrode appropriately placed within the external auditory canal out toward the auricular nerve branch, the neural stimulation circuit configured to deliver the neural stimulation signal with stimulation parameters effective to elicit depolarization of the auricular nerve branch from the appropriately placed neural stimulation electrode; and
    a controller connected to the neural stimulation circuit and adapted to control delivery of the neural stimulation signal from the neural stimulation circuit to control depolarization of the auricular nerve branch, the controller configured to provide a vagal stimulation therapy using controlled depolarization of the auricular nerve branch.

2. The device of claim 1, further comprising a feedback circuit connected to the controller to provide the controller with a feedback signal indicative of a physiologic signal, the controller being adapted to respond to the feedback signal to adjust the neural stimulation signal delivered from the neural stimulation circuit.

3. The device of claim 2, wherein the feedback circuit includes a heart rate monitor to detect a heart rate, and the controller is adapted to adjust the neural stimulation delivered from the neural stimulation circuit based on the detected heart rate.

4. The device of claim 3, wherein the heart rate monitor includes a sensor to directly detect a heart rate from a carotid artery.

5. The device of claim 2, wherein the feedback circuit includes a blood pressure monitor to detect a blood pressure, and the controller is adapted to adjust the neural stimulation delivered from the neural stimulation circuit based on the detected blood pressure.

6. The device of claim 5, wherein the blood pressure monitor is adapted to sense blood pressure from a carotid artery.

7. The device of claim 2, wherein the feedback circuit includes an electrocardiogram (ECG) monitor to detect an ECG signal, and the controller is adapted to adjust the neural stimulation delivered from the neural stimulation circuit based on the detected ECG signal.

8. The device of claim 1, wherein the controller is adapted to respond to provide open-loop neural stimulation based on predetermined neural stimulation parameters.

9. The device of claim 8, wherein the open-loop neural stimulation includes intermittent neural stimulation.

10. The device of claim 8, wherein the open-loop neural stimulation includes periodic neural stimulation.

11. The device of claim 1, wherein the neural stimulation circuit and the controller are adapted to provide a post myocardial infarction therapy using the neural stimulation signal delivered by the neural stimulation circuit to depolarize the auricular branch of the vagus nerve.

12. The device of claim 1, wherein the neural stimulation circuit and the controller are adapted to provide angina therapy using the neural stimulation signal delivered by neural stimulation circuit to depolarize the auricular branch of the vagus nerve.

13. The device of claim 1, further comprising an actuator to allow a patient to initiate delivery of the neural stimulation signal.

14. The device of claim 13, wherein the actuator includes a switch to be actuated by a magnetic field such that the patient provides the magnetic field to actuate the switch and initiate delivery of the neural stimulation signal to the neural stimulation electrode.

15. A device, comprising:
    a lead with a transcutaneous neural stimulation electrode to be placed behind an outer ear to target an auricular nerve branch with transcutaneous stimulation, wherein the auricular nerve branch innervates skin over a mastoid process behind the outer ear;

a neural stimulation circuit connected to the lead to deliver a neural stimulation signal adapted to stimulate the auricular nerve branch using the neural stimulation electrode;

a controller connected to the neural stimulation circuit and adapted to control delivery of the neural stimulation signal from the neural stimulation circuit to depolarize the auricular nerve branch to provide a vagal stimulation therapy; and a feedback circuit connected to the controller to provide the controller with a feedback signal indicative of a physiologic signal, the controller being adapted to respond to the feedback signal to adjust the neural stimulation signal delivered from the neural stimulation circuit.

16. The device of claim 15, wherein the feedback circuit includes a heart rate monitor to detect a heart rate, and the controller is adapted to respond to adjust the neural stimulation delivered from the neural stimulation circuit based on the detected heart rate.

17. The device of claim 16, wherein the monitor includes a sensor to directly detect a heart rate from a carotid artery.

18. The device of claim 15, wherein the feedback circuit includes a blood pressure monitor to detect a blood pressure, and the controller is adapted to respond to adjust the neural stimulation delivered from the neural stimulation circuit based on the detected blood pressure.

19. The device of claim 18, wherein the blood pressure monitor is adapted to sense blood pressure from a carotid artery.

20. The device of claim 15, wherein the feedback circuit includes an electrocardiogram (ECG) monitor to detect an ECG signal, and the controller is adapted to adjust the neural stimulation delivered from the neural stimulation circuit based on the detected ECG signal.

21. The device of claim 15, wherein the controller is adapted to respond to provide open-loop neural stimulation based on predetermined neural stimulation parameters.

22. The device of claim 21, wherein the open-loop neural stimulation includes intermittent neural stimulation.

23. The device of claim 21, wherein the open-loop neural stimulation includes periodic neural stimulation.

24. The device of claim 15, wherein the neural stimulation circuit and the controller are adapted to provide a post myocardial infarction therapy using the neural stimulation signal delivered by the neural stimulation circuit to depolarize the auricular branch of the vagus nerve.

25. The device of claim 15, wherein the neural stimulation circuit and the controller are adapted to provide angina therapy using the neural stimulation signal delivered by the neural stimulation circuit to depolarize the auricular branch of the vagus nerve.

26. The device of claim 15, further comprising an actuator to allow a patient to initiate delivery of the neural stimulation signal.

27. The device of claim 26, wherein the actuator includes a switch to be actuated by a magnetic field such that the patient provides the magnetic field to actuate the switch and initiate delivery of the neural stimulation signal to the neural stimulation electrode.

28. A device, comprising:
at least one port to connect at least one lead, the at least one lead including at least one neural stimulation electrode and at least one physiology sensor;
a neural stimulation circuit connected to the at least one port to selectively deliver a neural stimulation signal to the neural stimulation electrode to target an auricular nerve branch for neural stimulation, wherein the auricular nerve branch innervates surfaces of an outer ear and skin over a parotid gland and mastoid process near the outer ear, and wherein the neural stimulation electrode is configured to be appropriately placed proximate the auricular nerve branch to deliver stimulation toward the auricular nerve branch;

a feedback circuit connected to the at least one port to receive a feedback signal from the at least one physiology sensor; and a controller connected to the neural stimulation circuit and adapted to deliver the neural stimulation signal to the neural stimulation electrode, the controller further being connected to the feedback circuit and adapted to adjust the neural stimulation signal in response to the feedback signal.

29. The device of claim 28, wherein the feedback circuit includes a heart rate monitor to detect a heart rate, and the controller is adapted to adjust the neural stimulation based on the detected heart rate.

30. The device of claim 28, wherein the feedback circuit includes an electrocardiogram (ECG) monitor to detect an ECG signal, and the controller is adapted to adjust the neural stimulation based on the detected ECG signal.

31. The device of claim 28, wherein the feedback circuit includes a blood pressure monitor to detect a blood pressure, and the controller is adapted to respond to adjust the neural stimulation based on the detected blood pressure.

32. The device of claim 28, wherein the neural stimulation electrode includes a bipolar electrode adapted to be inserted into and appropriately placed within an external auditory canal proximate to the outer ear near the auricular nerve branch to stimulate the auricular nerve branch.

33. The device of claim 28, wherein the neural stimulation electrode includes a transcutaneous neural electrode adapted to be placed behind an ear to transcutaneously stimulate the auricular nerve branch.

34. The device of claim 33, wherein the transcutaneous neural electrode has a patch for adhering to skin.

35. The device of claim 28, wherein the neural stimulation electrode includes an electrode adapted to be pierced through skin to stimulate the auricular nerve branch.

36. The device of claim 28, wherein the neural stimulation electrode includes a subcutaneous cuff electrode.

37. The device of claim 28, further comprising a conductive housing, wherein the neural stimulation electrode includes the conductive housing.

38. A method to provide vagal stimulation, comprising:
positioning a non-invasive neural stimulation electrode proximate to an auricular nerve branch of a vagus nerve to target the auricular nerve branch for neural stimulation, including positioning a bipolar electrode past a conch of an outer ear into an external auditory canal, wherein the auricular nerve branch innervates surfaces of the outer ear and skin over a parotid gland and mastoid process near the outer ear, and wherein positioning the bipolar electrode in the external auditory canal includes placing the bipolar electrode within the external auditory canal effectively proximate to the outer ear near the auricular nerve branch to deliver stimulation from the external auditory canal out toward the auricular nerve branch; and applying a neural stimulation signal to the electrode appropriately placed within the external auditory canal to transcutaneously stimulate the auricular nerve branch from the external auditory canal.

39. The method of claim 38, wherein applying a neural stimulation signal to the electrode includes intermittently applying the neural stimulation signal in an open loop neural stimulation system.

40. The method of claim 38, wherein applying a neural stimulation signal to the electrode includes periodically applying the neural stimulation signal in an open loop neural stimulation system.

41. The method of claim 38, wherein applying a neural stimulation signal to the electrode includes adjusting the neural stimulation signal in a closed-loop neural stimulation system, the closed-loop neural stimulation system including a feedback signal indicative of a physiological signal.

42. The method of claim 41, further comprising sensing a heart rate to provide the feedback signal.

43. The method of claim 42, wherein sensing a heart rate includes sensing the heart rate from a carotid artery.

44. The method of claim 41, further comprising sensing a blood pressure to provide the feedback signal.

45. The method of claim 44, wherein sensing a blood pressure includes sensing the blood pressure from a carotid artery.

46. The method of claim 41, further comprising detecting an electrocardiogram (ECG) signal to provide the feedback signal.

* * * * *